US006946136B2

(12) United States Patent
Belshe et al.

(10) Patent No.: US 6,946,136 B2
(45) Date of Patent: Sep. 20, 2005

(54) TEMPERATURE-SENSITIVE AND COLD-ADAPTED HUMAN PARAINFLUENZA VIRUS TYPE 2 (HPIV-2) AND VACCINES BASED ON SUCH VIRUS

(75) Inventors: Robert B. Belshe, St. Louis, MO (US); Frances K. Newman, Collinsville, IL (US)

(73) Assignee: St. Louis University, St. Louis, MO (US)

( * ) Notice: Subject to any disclaimer, the term of this patent is extended or adjusted under 35 U.S.C. 154(b) by 993 days.

(21) Appl. No.: 09/785,764

(22) Filed: Feb. 16, 2001

(65) Prior Publication Data

US 2001/0029041 A1 Oct. 11, 2001

Related U.S. Application Data

(60) Provisional application No. 60/098,667, filed on Sep. 1, 1998.

(51) Int. Cl.[7] .............................................. A61K 39/12
(52) U.S. Cl. ..................... 424/204.1; 435/236; 435/237
(58) Field of Search ................................ 435/236, 237; 424/204.1

(56) References Cited

U.S. PATENT DOCUMENTS

| 3,927,209 A | | 12/1975 | Straub | |
|---|---|---|---|---|
| 5,869,036 A | * | 2/1999 | Belshe et al. | 424/93.2 |
| 6,165,774 A | * | 12/2000 | Cates et al. | 435/238 |

FOREIGN PATENT DOCUMENTS

| WO | WO 96/16672 A1 | 6/1996 |
|---|---|---|
| WO | WO 97/20468 A1 | 6/1997 |
| WO | WO 97/38138 A1 | 10/1997 |

OTHER PUBLICATIONS

Belshe et al., Journal of Medical Virology 10:235–242, 1982.*
Gross, et al. "Persistent Infection with Parainfluenza Type 3 Virus in Man." Am. Rev. Respir. Dis, 1973, pp. 894–898, vol. 108.
Downham et al. "Diagnosis and Clinical Significance of Parainfluenza Virus Infections in Children." Arch. Dis. Child, 1974, pp. 8–15, vol. 49.
Glezen, et al. "Effect of Passive Antibody on Parainfluenza Virus Type 3 Pneumonia in Hamsters." Infect. Immun., 1976, pp. 212–216, vol. 14.
Parkinson, et al. "Serological Evidence for Parainfluenza Virus Infection During Isolation at South Pole Station, Antarctica." Am. J. Epidemiol., 1980, pp. 334–340, vol. 112.
Sarkkinen, et al. "Type–Specific Detection of Parainfluenza Viruses by Enzyme–Immunoassay and Radioimmunoassay in Nasopharyngeal Specimens of Patients with Acute Respiratory Disease." J. Gen. Virol., 1981, pp. 49–57, vol. 56.

Belshe, et al. "Cold Adaption of Parainfluenza Virus Type 3: Induction of Three Phenotypic Markers." J. Med. Virol., 1982, pp. 235–242, vol. 10.
Welliver, et al. "Role of Parainfluenza Virus–Specific IgE in Pathogenesis of Croup and Wheezing Subsequent to infection." J. Pediatr., 1982, pp. 889–896, vol. 101.
Storey, et al. "Structural Characterization of Virion Proteins and Genomic RNA of Human Parainfluenza Virsus 3." J. Virol., 1984, pp. 761–766, vol. 52.
Crookshanks–Newman et al., "Protection of Weanling Hamsters from Experimental Infection with Wild–Type Parainfluenza Virus Type 3 (Para 3) by Cold–Adapted Mutants of Para3." J. Med. Virol., 1986, pp. 131–137, vol. 18.
Ray, et al. "Immunochemistry of Paramyxoviruses." IN "Immunochemistry of Viruses II" (M.V.H. Van Regenmortel and A.R. Neurath, eds.), 1990, pp. 215–236, Elsevier, Amsterdam.
Clements, et al. "Evaluation of Bovine, Cold–Adapted Human, and Wild–Type Human Parainfluenza Type 3 Viruses in Adult Volunteers and in Chimpanzees." J. Clin. Microbiol., 1991, pp. 1175–1182, vol. 29.
Matsouka, et al. "The PGene of Human Parainfluenza Virus Type 1 Encodes P and C Proteins but not a Cysteine–Rich V Protein." J. Virol., 1991, pp. 3406–3410, vol. 65.
Belshe, et al. "Evaluation of a Live Attenuated, Cold–Adapted Parainfluenza Virus Type 3 Vaccine in Children." J. Clin. Microbiol., 1992, pp. 2064–2070, vol. 30.
Hu, et al. "Functional Interactions Between the Fusion Protein and Hemagglutinin–neuraminidase of Human Parainfluenza Viruses." J. Virol., 1992, pp. 1528–1534, vol. 66.
Hall, et al. "A Cold–Adapted Mutant of Parainfluenza Virus Type 3 is Attenuated and Protective in Chimpanzees." J. Infect. Dis., 1993, pp. 958–962, vol. 167.
Henrickson, et al. "Epidemiology and Cost of Infection with Human Parainfluenza Virus Types 1 and 2 in Young Children." Clin. Infect. Dis., 1994, pp. 770–779, vol. 18.
Karron, et al. "A Live Human Parainfluenza Type 3 Virus Vaccine is Attenuated and Immunogenic in Healthy Infants and Children." J. Infect. Dis., 1995, pp. 1445–1450, vol. 172.
Collins, et al. "Parainfluenza Viruses." Fields Virology, Raven Press, 1996, pp. 1205–1241, vol. 1.

* cited by examiner

*Primary Examiner*—Laurie Scheiner
(74) *Attorney, Agent, or Firm*—Senniger Powers (57) ABSTRACT

The present invention relates to isolated, attenuated viral strains of human parainfluenza virus 2 (HPIV-2), which are useful in live vaccine preparations. These strains exhibit a temperature sensitive and cold adapted phenotype useful for stimulating a protective immune response in an inoculated mammal without producing severe symptoms.

37 Claims, 3 Drawing Sheets

FIG. 1

SPECIMEN 7255 ISOLATED FROM A 6 MONTH OLD CHILD
↓
10 PASSAGES IN AGMK AT 34°C
↓
10 PASSAGES IN FRhL AT 34°C
↓
6 PASAGES IN FRhL AT 30°C (cp 1-6)
↓
6 PASAGES IN FRhL AT 28°C (cp 7-12)
↓
8 PASAGES IN FRhL AT 26°C (cp13-20)
↓
13 PASAGES IN FRhL AT 24°C (cp21-33)
[C2450 cp27, C2768 cp33 SELECTED]

| C2450 | C2768 |
|---|---|
| ↓ | ↓ |
| 20 PASSAGES AT 23-24°C (cp28-47) | 30 PASSAGES AT 23-24°C (cp34-63) |
| ↓ | ↓ |
| C3440 (cp47) | C3490 (cp63) |
| ↓ | |
| C3605 (DIRECT SUBCLONE) | |

TEMPERATURE-SENSITIVE AND COLD-ADAPTED HUMAN PARAINFLUENZA VIRUS TYPE 2 (HPIV-2) AND VACCINES BASED ON SUCH VIRUS

CROSS-REFERENCE TO RELATED APPLICATION

This application is a continuation of International application Ser. No. PCT/US99/19929, filed Aug. 31, 1999, and claims the benefit of U.S. Provisional Application Ser. No. 60/098,667, filed Sep. 1, 1998, the entire contents of each of which is hereby incorporated herein by reference.

BACKGROUND OF THE INVENTION

The present invention relates to isolated, attenuated viral strains of human parainfluenza virus 2 (HPIV-2), which are useful in live vaccine preparations. These strains exhibit a temperature sensitive and cold adapted phenotype useful for stimulating a protective immune response in an inoculated mammal without producing the severe symptoms caused by the wild type virus.

The human parainfluenza viruses (HPIV), types 1, 2, and 3, are important pathogens in infants and young children. HPIV routinely causes otitis media, pharyngitis, and the common cold. These upper respiratory tract infections (URI) occur commonly and may be associated with lower respiratory infections (LRI) including croup, pneumonia, and bronchiolitis. Primary infection in young children is associated with lower respiratory disease and often leads to hospitalization. As a group, the parainfluenza viruses are the second most common cause of hospital admission for respiratory infection and are second only to respiratory syncytial virus as a significant pathogen in young children. Parainfluenza type 3 is unique among the parainfluenza viruses in its ability to commonly infect young infants less than 6 months of age. Bronchiolitis and pneumonia are common in infants infected with this type; in this regard, HPIV-3 is similar to respiratory syncytial virus. A number of reviews on HPIV have recently been published (Ray and Compans, 1990; Kingsbury, 1991; Henrickson et al., 1994) concerning the various aspects of these virus infections.

HPIV-2 infection occurs in yearly outbreaks in the United States (Downham et al., 1974). This pathogen has a peak incidence in the fall to early winter with a slightly longer "season" than HPIV-1. Croup is the most frequent LRI caused by this virus, but it can also cause any of the other respiratory illnesses associated with HPIV-1. The peak incidence of HPIV-2 infections occurs in the second year of life with approximately 60% of infections taking place in children less than 5 years of age. Of interest is the observation in one study that more girls than boys were symptomatic with LRI caused by HPIV-2, than LRI caused by HPIV-1 or 3 (Downham et al., 1974). LRI caused by HPIV-2 has been reported less frequently than with HPIV-1 and HPIV-3. Recent reports have indicated that either geographic differences or differences in isolation and detection techniques may play a role in under-reporting this virus (Downham et al., 1974; Henrickson et al., 1994). It has been estimated that during the 1991 epidemic, as many as 157,000 children under the age of 5 were seen in emergency rooms, and 35,000 children were admitted to hospitals in the United States with HPIV-2 infection. This epidemic resulted in almost $200 million of direct patient care costs for HPIV-1 and -2 combined.

All of the human parainfluenza viruses are very similar in structural, physicochemical, and biological characteristics.

A prototypic HPIV virion is composed of a single RNA strand of negative polarity surrounded by a lipid envelope of host cell origin. These are pleiomorphic, or multi-formed, viruses which have an average diameter of 150 to 250 nm. The typical HPIV genome contains approximately 15,000 nucleotides of genetic information (Storey et al., 1984) and encodes at least six viral proteins (3"-NP-P(+C)M-F-HN-L-5') (Storey et al., 1984). In addition, HPIV-1, 2, and 3 encode an additional nonstructural protein, "C," and HPIV-2 a protein "V." These proteins are produced from overlapping reading frames within the P gene and may require editing of the mRNA (Matsuoka et al., 1991). The complete nucleotide sequence of the HPIV-2 genome has not been published.

The human parainfluenza viruses are classified within the genus Paramyxoviridae. There are five major serotypes within this genus: the HIPV's 1–4, and mumps. The HPIV serotypes can be grouped antigenically into two divisions: (1) HPIV-1 and HPIV-3, within the genus Paramyxovirus, and (2) HPIV-2 and HPIV-4, within the genus Rubulavirus (Collins et al., 1996). HPIVs all share common antigens and variable levels of heterotypic antibody are often detected during infection. Thus, it is difficult to determine whether the heterotypic responses are reflective of past infections, or simply are cross reactions to similar antigens during serologic testing. However, specific hyperimmune animal serum in the past and, more recently, monoclonal antibodies have been employed to differentiate these viruses in standard assays (Sarkkinen et al., 1981).

Mucous membranes of the nose and throat are the initial site of parainfluenza virus infection. Patients with mild disease may have limited involvement of the bronchi as well. The larynx and upper trachea are involved in more extensive infections with HPIV-1 and HPIV-2, and result in the croup syndrome. Infections may also extend to the lower trachea and bronchi, with accumulation of thickened mucus and resultant atelectasis (incomplete lung expansion) and pneumonia. The possible contribution of the immune response to the pathogenesis of this illness is suggested by the observation that infants and children who develop parainfluenza virus croup produce local, virus-specific IgE antibodies earlier and in larger amounts than patients of comparable age who develop infections restricted to the upper respiratory tract (Welliver et al., 1982). Cell-mediated immune responses to parainfluenza viral antigens, as well as parainfluenza virus-specific IgE antibody responses, have been reported to be greater among infants with parainfluenza virus bronchiolitis than among infected infants who develop only upper respiratory illnesses. A prolonged carrier state of HPIV-3 is observed in patients with chronic bronchitis and emphysema (Gross et al., 1973). It has been suggested that healthy adults may shed infectious viruses intermittently and infect susceptible individuals; furthermore, investigators have also suggested that persistent infection might occur (Parkinson et al., 1980).

The hamster provides a recognized animal model for HPIV infection. Infected animals develop recognizable pathologic changes in the lung which are not altered by passive administration of antibodies (Glezen and Femald, 1976). Infected hamsters do not show visible signs of respiratory illness or a significant weight loss during infection. In addition, monkeys may be used as an animal model of infection, as demonstrated in the Examples 4–6, below.

A variety of vaccines have been developed over the years to prevent various viral infections in animals and humans. Two principal types of vaccines have been used: killed viruses and attenuated live virus. A killed virus is typically inactivated by chemical or physical treatment, but is generally less effective in stimulating a lasting immune response than an attenuated live virus. Attenuated live viruses are typically more effective, but may revert back to their virulent state while in the body. The time and cost involved in developing either killed or live vaccines is significant.

Live, attenuated vaccines may be obtained directly from progeny viruses isolated from infected animals. For example, U.S. Pat. No. 3,927,209 discloses a parainfluenza type-3 vaccine isolated as a virus strain from a bovine respiratory tract. Live attenuated vaccines may also be obtained by repeatedly cold passaging a wild-type strain through suitable cultures until the virus has lost its original pathogenic properties. A "cold passage" is the growth of a virus through an entire life cycle (infection of the host cell, proliferation in the host cell, and escape from the host cell) at a temperature lower than that in which the virus normally replicates. For example, cp45, a cold-adapted, temperature sensitive strain was obtained by passing the wild-type virus (JS strain) of HPIV-3 45 times at reduced temperatures. (Belshe and Hissom, 1982). The temperature sensitive cp45 strain is currently under evaluation for use as a candidate vaccine for HPIV-3 in humans. (Karron et al. 1995; Hall et al. 1993; Belshe et al. 1992; Clements et al. 1991; Crookshanks-Newman and Belshe 1986). Recent evaluation in children has revealed the cp45 strain to be highly attenuated and effective in stimulating an immunogenic response. (Karron et al. 1995; Belshe et al. 1992). Although cold passaging techniques have also been used to produce Influenza A and B vaccine strains, no similar successful cold passaging of an HPIV-2 virus has been described.

Attenuation in a particular vaccine strain is commonly evaluated with respect to three phenotypes of the strain: cold adaptation, temperature sensitivity and plaque size or yield in tissue culture. Cold adaptation (ca) relates to the ability of the virus to grow at reduced temperatures around 25° C. and temperature sensitivity (ts) relates to whether such growth is inhibited at temperatures around 40° C. Plaque titers are an assay for quantitatively evaluating the extent of virus growth, and are commonly used to evaluate the extent of cold-adaptive and/or temperature sensitive phenotypes. Other methods for determining whether vaccine is attenuated involve administering the vaccine to primates. For example, the attenuation of new polio vaccine lots is typically tested in monkeys before being approved for sale by the FDA.

Given the propensity of HPIV-2 disease to cause severe respiratory distress in infants and young children, a vaccine which would prevent severe infection, and the resulting necessity for hospitalization and treatment, is very desirable. Although the need for an HPIV-2 vaccine has been recognized for over two decades, and despite successes in isolating vaccine strains for HPIV-3 in the early 1980's, there is currently no vaccine available to immunize children against HPIV-2. Prior to the discovery of the applicants, HPIV-2 had not been successfully cold passaged. The difficulty in isolating attenuated strains of the HPIV-2 virus, as compared to the HPIV-3 virus, can be explained by the considerable morphological and phenotypic differences between the two viruses. Although they are antigenically similar, HPIV-2 is much more difficult to adapt to in vitro growth conditions and reduced temperatures than HPIV-3.

SUMMARY OF THE INVENTION

Therefore, it is an object of the invention to provide vaccine strains of HPIV-2 which may be used to immunize mammals, including humans, against wild-type HPIV-2 infection. It is a further object of the invention to provide vaccine strains which are greatly reduced in symptoms produced by the vaccine strain infection, as compared to infection with a wild-type HPIV-2 virus strain. It is a further object of the invention to provide a vaccine strain of HPIV-2 which will generate a protective immune response in the patient to whom it is administered.

Applicants have developed and isolated cold adapted vaccine strains of HPIV-2 from the Saint Louis University wild type strain of HPIV-2 designated SLU 7255. Several attenuated strains have now been isolated which have the desirable phenotype of cold adaptation and temperature sensitivity.

Thus, the present invention is drawn to isolated, attenuated strains of HPIV-2 virus which exhibit the phenotypic properties of cold adaptation and temperature sensitivity. Preferred isolated strains with these characteristics are those designated C3396, C3464, C3490, C3440, and C3444. More preferred isolated strains are those designated C3464, C3490, and C3440. In addition, the present invention is drawn to isolated, attenuated strains of HPIV-2 which exhibit the cold adapted and temperature sensitive phenotypes which are progeny or sub-clones of the isolated strains designated C3396, C3464, C3490, C3440, and C3444.

In addition, the present invention is drawn to vaccine compositions for use as live, attenuated vaccines which comprise any of the HPIV-2 viral strains described above and a pharmaceutically acceptable carrier. These compositions may also include any pharmaceutically acceptable excipients, diluents, and/or adjuvants.

The present invention is also drawn to a method of producing a protective immune response in a mammal by inoculating the mammal with a live, attenuated viral strain of the present invention.

DETAILED DESCRIPTION OF THE INVENTION

Figure 1:
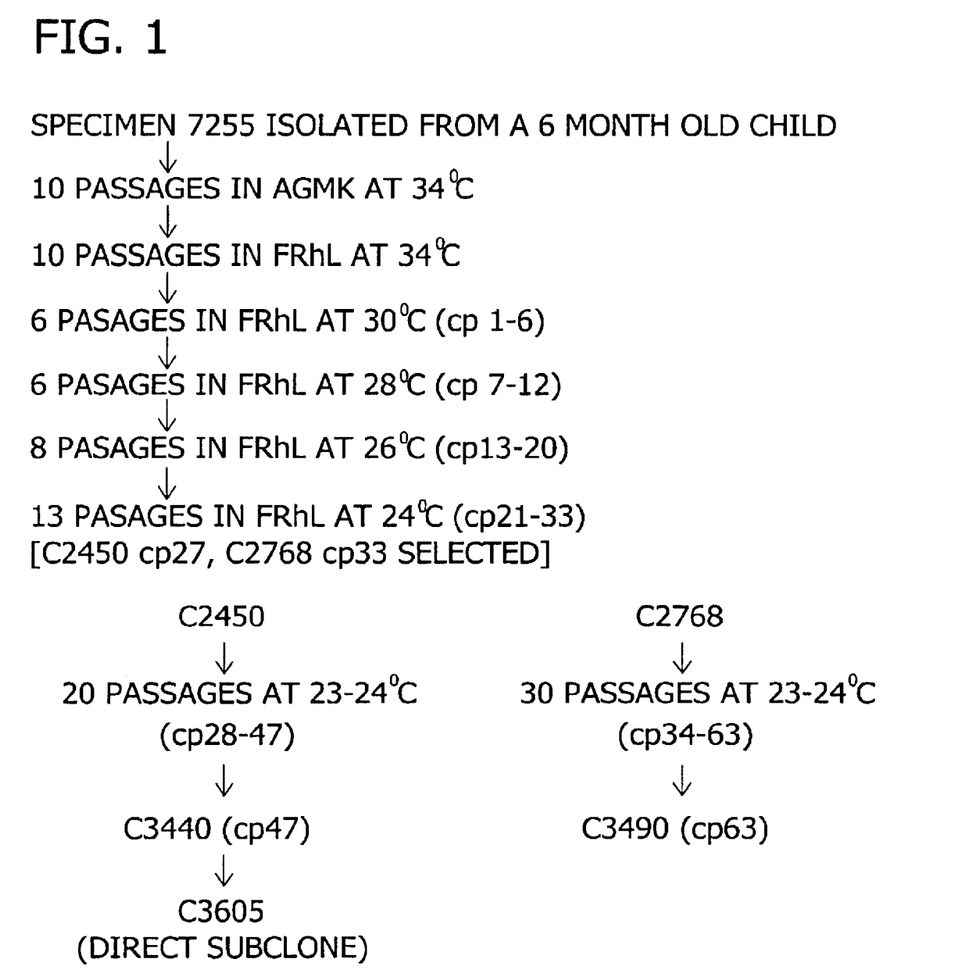
FIG. 1: A cold passaging diagram showing the lineage of isolated viral strains C3440 and C3490, described in the specification.

Unlike HPIV-3, wild-type strains of HPIV-2 which can be successfully cultured and maintained in vitro have proven difficult to isolate. Applicants tested over fifty strains of wild-type virus collected from various sources before discovering a wild type strain which could be successfully maintained in in vitro culture. As shown in the disclosure below, applicants have developed isolated temperature sensitive (ts) and cold adapted (ca) viral strains from non-temperature sensitive and non-cold adapted wild type (wt) HPIV-2 viral strains. As shown in FIG. 1, applicants successfully modified the wild type strain of HPIV-2 to grow at reduced temperatures, creating strains preferably adapted to less than 30° C., more preferably to less than 26° C., and most preferably to less than about 24° C. These cold adapted strains are then assayed to confirm that they are appropriately temperature sensitive. Applicants have discovered that a fraction of the cold adapted strains will exhibit temperature sensitivity to the degree necessary to prevent viral growth and proliferation in the lower respiratory tract, and the accompanying severe symptoms of HPIV-2 illness. The combination ca and ts phenotypes of these developed strains make them excellent attenuated strains for use as live vaccine against HPIV-2 infection, as they are able to grow without restriction at cooler production temperatures, and are attenuated in the patient to whom they are administered.

Although a particular HPIV-2 wild type strain was used for developing the strains disclosed below, it is believed that any wild type strain which can be maintained as an in vitro culture may be used to develop a ts and ca attenuated strain of HPIV-2 using the methods demonstrated by the applicant. Fetal Rhesus monkey lung (FRhL-2) cells are preferred as hosts for cold-passaging, as they are well characterized cells used in vaccine studies. However, other cultured mammalian host cells are contemplated for use in producing the attenuated viral strains of the present invention. Likewise, one of skill in the art may choose to modify the cold passaging technique, using different temperatures or numbers of cold passages at each temperature. However, such modification would preferably maintain gradually stepped temperatures, similar to those described by the applicants below.

Strain SLU 7255 of parainfluenza virus type 2 (HPIV-2) was isolated from a 6 month old child hospitalized with croup and pneumonia (deposited with the ATCC, Accession No. PTA-1474). Although it was originally isolated in primary Rhesus monkey kidney (RMK) cells, SLU 7255 was adapted to grow in fetal Rhesus lung (FRhL-2) cells, a diploid cell line used for vaccine studies. Following adaption to the FRhL cells, SLU 7255 was serially passaged in the cold ($\leq 30°$ C.) to produce vaccine candidates in a similar fashion to the JS strain of HPIV-3, described in Belshe and Hissom, 1982, incorporated herein by reference. The wild type strain was first passaged 6 times at 30° C., then 6 times at 28° C., then 8 times at 26° C., then 13 times at 24° C. See FIG. 1 for a diagram of the cold passaging process. Applicants were surprised to find that the cold-passaging temperature had to be stepped down gradually in order to successfully adapt HPIV-2 virus, unlike HPIV-3, which can be immediately cold passaged at 22° C. After cold adaptation, clones were selected by passing a Pasteur pipet through an agarose overlay using a standard plaque assay technique in primary African green monkey kidney (AGMK) cells, aspirating the agar plug, and inoculating the clone into a tissue culture tube containing primary AGMK cells. After a primary screening of clones, clones C2450 and C2768 were further cold passaged about 18–30 times at 23°–24° C. to yield the isolated clones C3464 (deposited with the ATCC, Accession No. PTA-1471), C3440, and C3490 (deposited with the ATCC, Accession No. PTA-1473). Additionally, C3605, which is a plaque purified clone of C3440, has been deposited with the ATCC, Accession No. PTA-1472. No successful cold passaging of the HPIV-2 virus had previously been disclosed.

To determine if the HPIV-2 clones were temperature sensitive, the titers of each clone at 32° C. and 39° C. were compared using the hemadsorption plaque assay. A clone is considered to be "temperature sensitive" when it exhibits a $\geq 100$-fold decrease in titer at 39° C. compared with its titer at 32° C., and, conversely, is considered to be a wild type virus if it exhibits <100-fold decrease in titer at 39° C. compared with 32° C. More preferably, a clone has a titer of <1.0 pfu/ml at 39° C. The results of the ts phenotyping using the hemadsorption screening assay showed that the majority of the clones tested exhibited the ts phenotype.

To determine if clones possessed the cold-adapted property, their growth at 23° C. was compared with their growth at 32° C. See Table 1. Each of the clones was inoculated onto tissue culture tube monolayers of either Vero cells or primary AGMK cells (data not shown) and incubated at either 23° C. or at 32° C. Tube cultures were harvested from each of the clones on day 7 and day 14 post inoculation when incubated at 23° C. and on day 7 post inoculation when they were incubated at 32° C. The titer of virus in culture supernatants was determined by plaque assay at 32° C. on Vero cells. Plates were visualized by staining the cells with hematoxylin and eosin after 5 days. A clone which had a titer at 23° C. that was within one hundred fold of its titer at 32° C. was considered to be cold adapted (ca).

Six of the clones tested were cold adapted, however, one of them, C3252, did not grow at either temperature. In contrast to the cold adapted clones (C3396, C3464, C3490, C3457, C3440, and C3444), the wild type parent control, Pool 453, did not grow in Vero cells at 23° C.

Efficiency of plaquing (EOP) assays were performed to determine the cut-off temperature of each clone. Each vaccine candidate was analyzed for its ability to produce plaques on Vero cells at 32° C., 36° C., 37° C., 38° C., and 39° C. See Table 2. C3464, C3490, C3457, C3440 and C3444 exhibited a cut-off temperature of 38° C. while two of the clones (C3396 and C3444) were 1000-fold restricted in growth at 39° C. compared with their growth at 32° C.

Clones other than C3396, C3464, C3490, C3457, C3440, and C3252 which are developed and isolated from wild type HPIV-2 virus in a manner similar to that disclosed by the applicant and which also exhibit the ts and ca phenotype are within the scope of the present invention. Following the examples and teachings set forth in this specification, one of ordinary skill in the art would be able to develop and isolate ts and ca clones from wild type HPIV-2 virus using routine methods. Additionally, it is well within the ordinary skill of a practitioner in the art of virology to further cold passage sub-clones of the disclosed preferred strains, or to adapt these strains for culture in other host cells by utilizing established methods. Thus, subclones and progeny of the above preferred strains are also within the scope of the present invention.

As shown in the examples below, the isolated viral strains of the present invention are useful in vaccine compositions for inducing a protective immune response in mammals. An isolated, attenuated HPIV-2 viral strain of the present invention is preferably administered as a live vaccine in an effective amount which will allow some growth and proliferation of the virus, in order to produce the desired immune response, but which will not produce HPIV-2 disease symptoms. The proper amount of the virus to use in the live vaccine will depend on several factors, including: the virulence or hardiness of the particular isolated, attenuated HPIV-2 strain; the age of the patient to whom the vaccine will be administered; the body mass and general health of the patient to whom the vaccine will be administered; and whether the immune system of the patient to whom the vaccine will be administered is compromised.

The isolated, attenuated strains of HPIV-2 of the present invention may be formulated into vaccine compositions for administration to the patient by any usual route (as an intraperitoneal or intravenous injection, topically applicable formulation, formulation of oral administration, etc.), but is most preferably formulated as a spray or wash for application to the mucosa of the upper respiratory tract. Such application will assist in stimulating local mucosal immunity, which will offer greater protection against later infection by the HPIV-2 wild type virus. Such vaccine formulations comprise the isolated, attenuated virus of the present invention and a pharmaceutically acceptable carrier, such as sterile saline. In addition, the vaccine formulation may comprise pharmaceutically acceptable excipients, diluents, and/or adjuvants which will aid in producing a protective immune response in the patient. Excipients which may be used in vaccine formulations of the present invention include agents which will help the virus adhere to the mucosa and spread along the surface of the upper respiratory tract, such as gums or starches.

Isolated, attenuated strains of HPIV-2 of the present invention may be administered in vaccine formulations to mammalian patients in order to elicit a protective immune response. After vaccination, the immune system of the patient will exhibit a primed immune response to challenges with a wild-type HPIV-2 virus, moderating the severity of HPIV-2 infection and illness. Although the vaccine strains of the present invention are intended for use with human patients, use with other mammals which exhibit deleterious symptoms with HPIV-2 infection is also contemplated within the scope of the invention. The vaccine strains of the present invention are preferably administered to the patient at a young age in order to prevent more severe HPIV-2 infections, which often occur in infancy. Although it is currently anticipated that a single administration of the vaccine strain of the present invention will be sufficient to induce a primed immune response to later challenges with the wild-type HPIV-2 virus, more than one administration may be indicated based on factors similar to those for dosage, listed above. One of ordinary skill in the art would be able to devise the proper dosing regimen for a particular patient without undue experimentation.

Several examples of the use of the isolated, attenuated HPIV-2 strains of the present invention are illustrated below. It should be appreciated that these are offered as illustrations of the invention, and are not meant to limit the embodiments of the invention in any way.

EXAMPLE 1

Based on their phenotypic characteristics, 3 of the ts and ca clones, C3440, C3464, and C3490, were chosen for evaluation in hamsters. Table 3 illustrates the ts and ca phenotype of these selected clones and the wild type parent of these HPIV-2 vaccine candidates. Weanling hamsters were deeply anesthetized and intranasally inoculated with either the parent wild type virus or one of the vaccine candidates. The titer of the inoculum received by the hamsters is shown in Table 4. Each animal received a total inoculum of 0.1 ml (0.05 ml/nostril) using a micropipettor with aerosol resistant pipet tips to avoid cross contamination. Groups of twenty hamsters were inoculated with one of the vaccine candidates or the wild type parent virus. Four hamsters from each group were euthanized at five time points, day 1, 2, 3, 4, and 7 post inoculation. Ten uninoculated animals were euthanized (2 at each of the five time points) as a control group. Blood was collected by cardiac puncture and the lungs and nasal turbinates were removed from each animal on the day of harvest. Each tissue homogenate was tested for virus by plaque assay on Vero cells at 32° C. for five days. The Vero monolayers were fixed with formaldehyde and stained with hematoxylin and eosin to visualize virus plaques.

Figure 2:
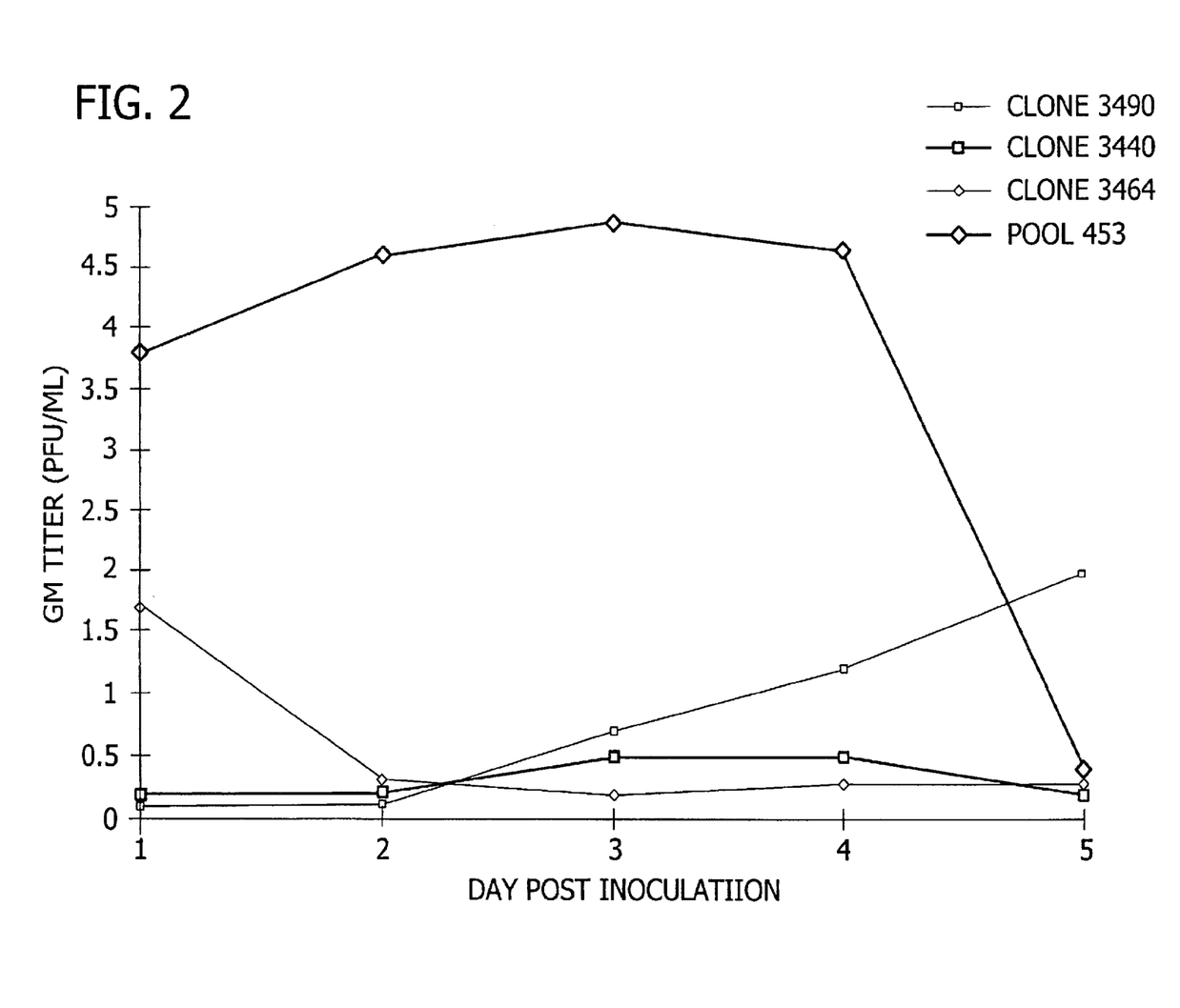
FIG. 2: This graph shows the active viral titers of nasal washes collected from hamsters which have been inoculated with strain C3490 (■), C3440 (□), C3464(♦), or the wild type strain, pool 453 (◇).
Figure 3:
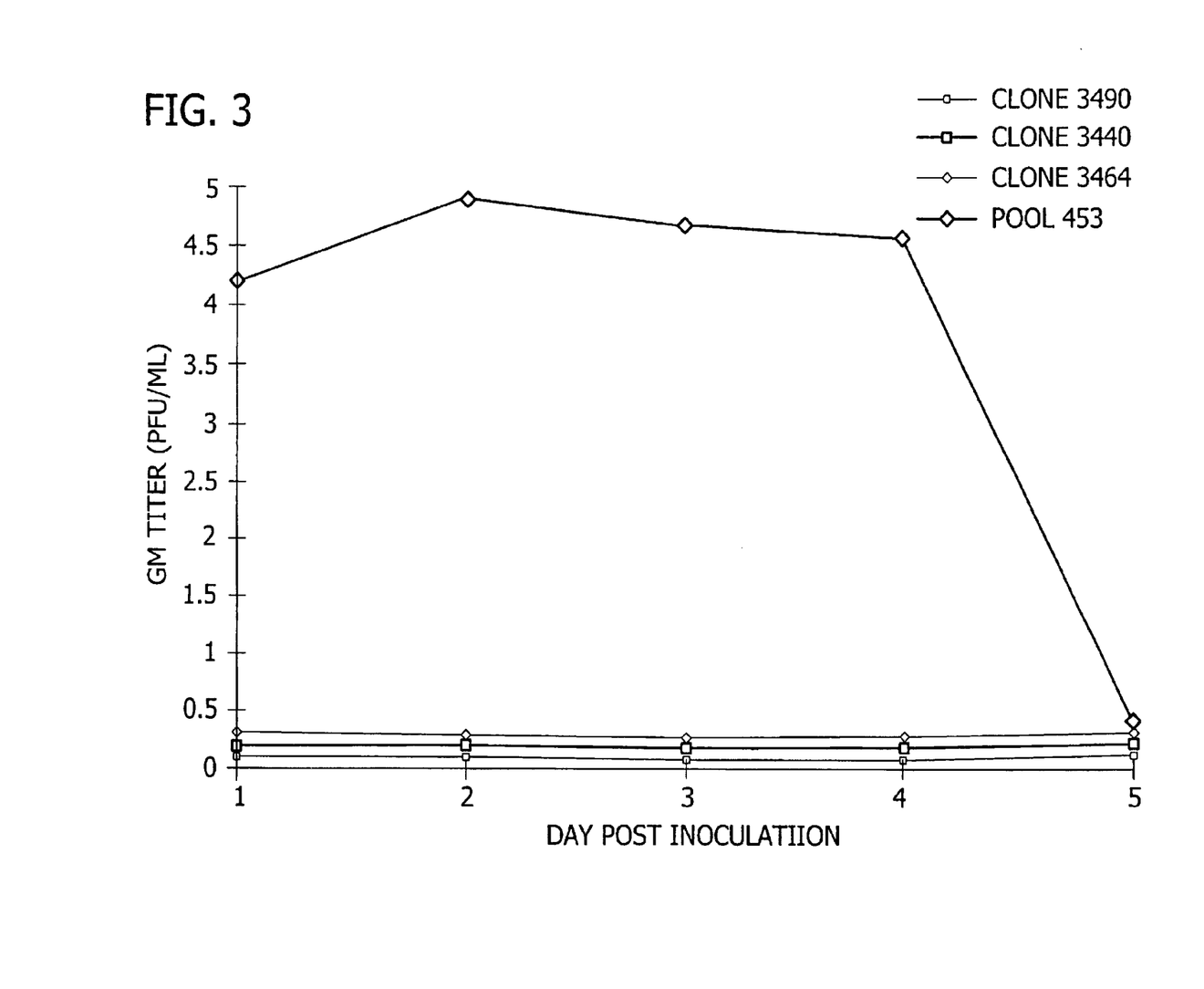
FIG. 3: This graph shows the active viral titers of bronchial/lung washes collected from hamsters which have been inoculated with strain C3490 (■), C3440 (□), C3464 (♦), or the wild type strain, pool 453 (◇).

The wild type parent HPIV-2 grew equally well in both the nasal turbinates and the lungs of the weanling hamsters (See FIGS. 2 and 3). The duration of virus shedding was 4 days with a peak titer of 5.5 pfu/gm of tissue (all pfu/gm values in these examples are in $\log_{10}$) in the nasal turbinates on day 3 and a mean peak titer of 5.2 pfu/gm of tissue in the lungs on day 2. Clone 3490, cp51, was shed from day 3 through day 7 in the nasal turbinates of the hamsters. The mean peak titer of C3490 was 4.5 pfu/gm of tissue recovered on day 7. HPIV-2 was recovered from only a few animals inoculated with C3440 or C3464 indicating that the clones were minimally infectious. Virus was not recovered from the lungs of any animals inoculated with one of the three cold adapted clones. These three cold adapted temperature sensitive clones were attenuated in hamsters and may be used for additional in vivo characterization.

EXAMPLE 2

Each of the clones evaluated in hamsters were also tested for genetic stability in vitro. We performed a stress test on each of the clones by serially blind passing each of them once each week for four weeks at the permissive temperature (32° C.), an intermediately permissive temperature (35° C.), and the restrictive temperature (39° C.) to determine if the viruses would revert to the wild type phenotype under selective pressure against the ts phenotype. The results of the stress test are shown in Table 5. After each passage, the virus was titered at 32° to 39° C. to detect changes in the ts phenotype. Each of the clones retained their ts phenotype after serial passage at 39° C. indicating that they are genetically stable.

In addition to the stress test we selected plaques from each of these three cold passaged viruses to determine if there was a mixture of virus phenotypes within the virus pools (Table 6). Each of the 10 subclones selected from Pool 474 (clone 3490) were clearly ts and exhibited a complete cutoff at 39° C. Two of the 10 subclones from Pool 477 (clone 3440) exhibited some growth at 39° C. but had titers of at least 100-fold less at 39° C. compared with 32° C. All 6 of the subclones of Pool 484 (clone 3464) had a complete cutoff at 39° C. and retained their ts phenotype. These results indicate that clone 3490 and clone 3464 have a single phenotype in contrast to clone 3440 which has a mixture of phenotypes. We selected a subclone (C3605) from C3440 in order to have a more homogenous vaccine candidate.

EXAMPLE 3

Three clones of SLU 7255 which emerged as the most promising vaccine candidates, C3464 (cp50), C3490 (cp63), and C3605 (cp47, a subclone of C3440). These three were evaluated in seronegative Rhesus monkeys. Pools of virus were prepared in Vero cells for each of the clones and the wild type virus. Titers of the pools used in the following examples are shown in Table 7.

EXAMPLE 4

The objective of the this experiment was to evaluate the ability of wild type (wt) HPIV2 to infect seronegative rhesus monkeys. Each of the rhesus monkeys involved in this and the two following experiments was selected based on their serum HAI antibody status against wild type HPIV2. Monkeys were considered to be eligible for inclusion if they had an HAI antibody titer of <1:8 to wild type HPIV2 antigen. A total of 20 rhesus monkeys have been involved with the three experiments. Sixteen of them received either the wild type HPIV or one of two ca/ts vaccine candidates and the other 4 animals received placebo. Two of the 4 monkeys participated as placebo animals in more than one experiment. Each experiment had two placebo control animals.

Pools of the wild type HPIV2 parent and the ca/ts clones, C3490 and C3605, were prepared in Vero cells. C3605 is a subclone of isolated strain C3440. The staff at New Iberia diluted the viruses at the time of inoculation for the first two experiments but we changed the procedure when the titration of the post inoculum of Example 5 was determined to be $\leq 2.0$ pfu/ml when it was supposed to be 6.0 pfu/ml. The inoculum for Example 6, both the ca/ts vaccine candidate C3605 and the wild type HPIV2 challenge virus, were prepared at Saint Louis University and shipped frozen to New Iberia at the intended dose.

Nasal wash (NW) samples and bronchial lavage (BL) samples were collected from each of the monkeys on day 0 (prior to inoculation) and on days 3, 5, 7, 10, 12, 14, 17, 19, and 21 following intranasal and intratracheal inoculation of 105.5 pfu of virus or placebo. Samples were mixed with transport media, aliquoted, snap—frozen in a dry ice/alcohol bath, and stored at −70° C. Serum samples were collected from each monkey prior to inoculation and on day 7, 14, 21, 28, 42, and 56 following inoculation.

Samples were inoculated into duplicate primary rhesus monkey kidney tissue culture tubes and incubated at 32° C. RMK tubes were hemadsorbed at days 5, 9, and 14 with Guinea pig erythrocytes. Hemadsorption positive tubes were identified using immunofluorescence (IF). Each sample was also quantified by plaque assay on Vero cell monolayers at 32° C. Serum samples were tested for antibody to wild type HPIV2 by hemagglutination inhibition (HAI). All samples were tested in the same assay following treatment with receptor destroying enzyme (RDE) and heat activation.

Results: Wild type HPIV2 was recovered from the NW and BL samples of each of the four of the rhesus monkeys inoculated in the first experiment. See Table 8. Similar titers of HPIV2 were recovered from both the NW and BL samples with the mean peak titer of ≧1.73 pfu/ml on day 7 for NW samples and ≧1.53 pfu/ml on day 5 for BL samples. An HAI antibody response to wild type HPIV2 was observed in each of the 4 animals by day 21 following inoculation. Neither of the placebo recipients shed virus or had an HAI antibody response.

EXAMPLE 5

The purpose of this experiment was to determine the growth, attenuation, genetic stability, and immunogenicity of HPIV2 vaccine candidates in seronegative rhesus monkeys.

Two HPIV2 ca/ts vaccine candidates, C3490 and C3605, were tested. See Table 9A and 9B. We isolated virus from the nasal wash (NW) samples from each of the 4 monkeys who received C3490 although two of them shed for only one day each (95N148 and 95N139). We recovered virus from the NW of 3 of the 4 animals who received C3605 (Pool 502). One of the animals in the C3605 group, 95N152, shed virus on two days although this animal was seropositive (HAI titer=32) at the time of vaccination. The mean peak titer of virus recovered from the NW of animals shedding HPIV2 was 1.5 pfu/ml on day 7 for C3490 and 1.4 pfu/ml on day 7 for C3605. None of the 8 monkeys vaccinated with either C3490 or C3605 ca/ts HPIV2 vaccine candidates shed virus from the lower respiratory tract, i.e., from the bronchial lavage samples. HPIV2 was not isolated from either of the placebo recipients. Overall, the HAI data shows a minimal rise (<4 to 8) in two monkeys from the C3490 group (95N140 and 95N139) and a rise in monkey number 95N148 who went from an HAI titer of 8 on day 28 to a titer of 32 on day 42 and day 56. However, this monkey exhibited titers of 16 from day 0 through day 21, therefore the HAI titer increase from 8 to 32 may not represent a strong case for an antibody response.

There were no HAI antibody rises in the group who received C3605 or in the placebo recipients. Results of the back titration of an aliquot of the diluted vaccine indicated that the inoculum for this experiment was too low. The back titration of the post inoculum was determined to be approximately 1.0 pfu/ml for C3490 and 2.5 pfu/ml for C3605. From this data, one can see that the vaccine strains are attenuated in the lower respiratory tract.

EXAMPLE 6

The purpose of this experiment was to evaluate the efficacy of the a preferred attenuated HPIV2 vaccine candidate in seronegative rhesus monkeys. Four seronegative rhesus monkeys received intratracheal and intranasal inoculation of a pre-diluted dose of C3605. All 4 of the animals shed C3605 HPIV2 from their NW samples. See Table 10. Virus was not isolated from the BL of any animal that received the ca/ts vaccine candidate. The peak mean titer of vaccine shed from the NW samples was 1.88 pfu/ml on day 7. None of the monkeys exhibited an HAI antibody response to C3605 HPIV2. The placebo recipients did not shed virus or have an HAI antibody response.

Fifty-six days following their original vaccination with the ca/ts clone C3605, each of the four monkeys was challenged with a single inoculum of wild type HPIV2. See Table 11. The placebo recipients also received the wild type HPIV2 challenge virus. Virus was not recovered from any of the monkeys vaccinated with C3605; however, both of the animals that originally received the placebo and then were challenged with the wild type HPIV2 shed virus from both NW and BL samples. HAI antibody responses to the wild type HPIV2 challenge virus were very vigorous in 3 of the 4 monkeys that were vaccinated with C3605. HAI titers of ≧64 were evident by day 7 following challenge with the wild type HPIV2 virus. The fourth monkey, 95N024, seroconverted by day 28 following challenge. Animals that received placebo and then the challenge virus mounted an HAI antibody response similar to the monkeys in Example 4 who were inoculated with wild type HPIV2, i.e., both of the monkeys seroconverted by day 21 post challenge.

The foregoing descriptions of the preferred embodiments of the present invention have been presented for purposes of illustration and description. They are not intended to be exhaustive or to limit the invention to the precise form disclosed, and many modifications and variations are possible in light of the above teaching. Such modifications and variations which may be apparent to a person skilled in the art are intended to be within the scope of this invention.

TABLE 1

Characterization of the wild type parent and selected clones of PIV-2 (SLU 7255) for the cold adapted property.

| Clone # | Virus Titer (log pfu/ml) | | |
|---|---|---|---|
| | 23° C. D7 | 23° C. D14 | 32° C. D7 |
| C3252 | <2 | <2 | <2 |
| C3396 | 4.8 | 6.7 | 6.4 |
| C3464 | 3.1 | 5.3 | 6.8 |
| C3490 | 3.8 | 6.0 | 5.7 |
| C3457 | 4.0 | 6.4 | 6.2 |
| C3440 | 3.4 | 5.8 | 6.5 |
| C3444 | 3.8 | 5.7 | 5.3 |
| Pool 453 (Wild Type PIV-2) | <2 | <2 | 6.1 |

TABLE 2

Efficiency of plaquing (EOP) assay of the wild type parent (Pool 453) and selected clones of PIV-2 (SLU 7255)

| Clone # | cp Level | Virus Titer (pfu/mL) | | | | |
|---|---|---|---|---|---|---

TABLE 5-continued

Virus titers (log pfu/ml at 32° C.)

| Clone | week 1 | | | week 2 | | | week 3 | | | week 4 | | |
|---|---|---|---|---|---|---|---|---|---|---|---|---|
| | 32° C. | 35° C. | 39° C. | 32° C. | 35° C. | 39° C. | 32° C. | 35° C. | 39° C. | 32° C. | 35° C. | 39° C. |
| Pool 453 (wild type) | 7.5 | 5.7 | 2.9 | 5.5 | 4.1 | 2.2 | 3.8 | 3.2 | 2.2 | 5.3 | 4.1 | 3.1 |
| C3464 | 5.1 | 1.3 | <1 | <1 | <1 | <1 | 1.3 | <1 | <1 | <1 | <1 | <1 |
| C3490 | 5.5 | 2.4 | <1 | <1 | 2.0 | <1 | <1 | <1 | <1 | 4.2 | 1.0 | <1 |
| C3440 | 3.4 | <1 | <1 | <1 | <1 | <1 | <1 | <1 | <1 | <1 | <1 | <1 |
| Pool 453 (wild type) | 7.3 | 6.3 | 3.8 | 5.7 | 5.3 | 2.9 | 4.9 | 4.2 | 3.1 | 6.0 | 4.9 | 4.1 |

TABLE 6

Phenotype of PIV-2 subclones

| Parent Clone # | Sub-Clone # | Pool # | Virus Titer (log pfu/mL) | |
|---|---|---|---|---|
| | | | 32° C. | 39° C. |
| C3490 | C3591 | 474 | 4.4 | <1 |
| C3490 | C3592 | 474 | 5.4 | <1 |
| C3490 | C3593 | 474 | 5.3 | <1 |
| C3490 | C3594 | 474 | 7.0 | <1 |
| C3490 | C3595 | 474 | 6.2 | <1 |
| C3490 | C3596 | 474 | 6.7 | <1 |
| C3490 | C3597 | 474 | 6.3 | <1 |
| C3490 | C3598 | 474 | 7.4 | <1 |
| C3490 | C3599 | 474 | 6.8 | <1 |
| C3490 | C3600 | 474 | 5.8 | <1 |
| C3440 | C3601 | 477 | 7.2 | 3.1 |
| C3440 | C3602 | 477 | 6.9 | <1 |
| C3440 | C3603 | 477 | 7.3 | <1 |
| C3440 | C3604 | 477 | 6.6 | <1 |
| C3440 | C3605 | 477 | 7.3 | <1 |
| C3440 | C3606 | 477 | 6.6 | <1 |
| C3440 | C3607 | 477 | 7.1 | <1 |
| C3440 | C3608 | 477 | 7.1 | <1 |
| C3440 | C3609 | 477 | 4.7 | <1 |
| C3440 | C3610 | 477 | 6.7 | 4.4 |
| C3464 | C3621 | 484 | 5.5 | <1 |
| C3464 | C3622 | 484 | 6.0 | <1 |
| C3464 | C3623 | 484 | 5.5 | <1 |
| C3464 | C3625 | 484 | 6.2 | <1 |
| C3464 | C3627 | 484 | 6.9 | <1 |
| C3464 | C3628 | 484 | 7.0 | <1 |
| | control | 491 | 6.4 | 6.2 |

TABLE 7

Titers of wild type and attenuated pools of HPIV-2, SLU 7255, to be used for the inoculation of seronegative Rhesus monkeys.

| Pool # | Clone # | Cold passage level | Virus Titer (log pfu/ml) | |
|---|---|---|---|---|
| | | | 32° C. | 39° C. |
| 499 | C3464 | 50 | 5.4 | 2.0 |
| 500 | C3490 | 63 | 7.2 | 1.3 |
| 502 | C3605* | 47 | 7.8 | <1.0 |
| 504 | wild type | 0 | 6.4 | 6.6 |

*C3605 is a subclone of C3440

TABLE 8

Samples from Rhesus Monkeys Inoculated with wild type HPIV-2

| Rhesus Monkey ID# Pool 504 (wild type) | HPIV-2 Isolation from Vero Assay [Virus Titer(log pfu/mL)] | | | | | | | | | | | | HAI Titer | | | | | | |
|---|---|---|---|---|---|---|---|---|---|---|---|---|---|---|---|---|---|---|---|
| | Day Post Inoculation (NW[a]) | | | | | | Day Post Inoculation (BL[b]) | | | | | | Day Post Inoculation | | | | | | |
| | 0 | 3 | 5 | 7 | 10 | 12 | 0 | 3 | 5 | 7 | 10 | 12 | 0 | 7 | 14 | 21 | 28 | 42 | 56 |
| 95N002 | <1 | ≧1.5* | 2.1 | 3.0 | <1 | <1 | <1 | ≧1.5* | 1.6 | <1 | <1 | <1 | <4 | <4 | 16 | 32 | 64 | 64 | 64 |
| 95N055 | <1 | ≧1.5* | <1 | ≧1.5* | <1 | <1 | <1 | ≧1.5* | ≧1.5* | 1.0* | <1 | <1 | <4 | <4 | 8 | 32 | 32 | 16 | 16 |
| 95N059 | <1 | ≧1.5* | 1.0* | ≧1.5* | <1 | <1 | <1 | ≧1.5* | ≧1.5* | <1 | <1 | <1 | <4 | <4 | 4 | 16 | 16 | 16 | 8 |
| 95N060 | <1 | ≧1.5* | <1 | <1 | <1 | <1 | <1 | ≧1.5* | ≧1.5* | <1 | <1 | <1 | <4 | <4 | 8 | 8 | 16 | 16 | 16 |

TABLE 8-continued

Samples from Rhesus Monkeys Inoculated with wild type HPIV-2

| Rhesus Monkey ID# Pool 504 (wild type) | HPIV-2 Isolation from Vero Assay [Virus Titer(log pfu/mL)] | | | | | | | | | | | | HAI Titer | | | | | |
|---|---|---|---|---|---|---|---|---|---|---|---|---|---|---|---|---|---|---|
| | Day Post Inoculation (NW[a]) | | | | | | Day Post Inoculation (BL[b]) | | | | | | Day Post Inoculation | | | | | |
| | 0 | 3 | 5 | 7 | 10 | 12 | 0 | 3 | 5 | 7 | 10 | 12 | 0 | 7 | 14 | 21 | 28 | 42 | 56 |
| Placebo | | | | | | | | | | | | | | | | | | | |
| 95N003 | <1 | <1 | <1 | <1 | <1 | <1 | <1 | <1 | <1 | <1 | <1 | <1 | <4 | <4 | <4 | <4 | <4 | <4 | <4 |
| 05M-7 | <1 | <1 | <1 | <1 | <1 | <1 | <1 | <1 | <1 | <1 | <1 | <1 | <4 | <4 | <4 | <4 | <4 | <4 | <4 |

[a]NW = nasal wash
[b]BL = Bronchial Lavage
*= titer based on RMK data, one positive tube = 1.0, two HA positive tubes =≥ 1.5

TABLE 9

A: Virologic and Immunologic Results of Samples collected from Rhesus Monkeys Vaccinated with either C3490 or C3605 HPIV2 Vaccine Candidate

| Rhesus Monkey # | HAITiter,DayPost Inoculation[d] | | | | | | | HPIV-2 Isolation from NW[a] | | HPIV-2 Isolation from BL[b] | |
|---|---|---|---|---|---|---|---|---|---|---|---|
| | 0 | 7 | 14 | 21 | 28 | 42 | 56 | on RMK tubes (day) | on Vero plates (day) | on RMK tubes (day) | on Vero plates (day) |
| Pool 500 (PIV2, C3490, cp63) | | | | | | | | | | | |
| 95N140 | <4 | <4 | <4 | <4 | <4 | 8 | 8 | 5,7,10 | 5,7,10 | VNI | <1 |
| 95N159 | 4 | 8 | 8 | 4 | 8 | 8 | 8 | 7,14 | <1 | VNI | <1 |
| 95N148 | 16 | 16 | 16 | 16 | 8 | 32 | 32 | 17 | <1 | VNI | <1 |
| 95N139 | <4 | <4 | <4 | <4 | <4 | 8 | 4 | 17 | <1 | VNI | <1 |
| Pool 502 PIV2, C3605, cp47 | | | | | | | | | | | |
| 95N152 | 32 | 32 | 32 | 32 | 32 | 32 | 32 | 5,7 | <1 | VNI | <1 |
| 95N147 | 4 | 8 | 8 | 8 | 8 | 8 | 8 | 3,5,7,10,12 | 10,12 | VNI | <1 |
| 95N145 | <4 | <4 | <4 | <4 | <4 | <4 | <4 | 3,5,7,10 | 5,7,10 | VNI | <1 |
| 95N130 | <4 | <4 | 4 | 4 | 4 | 4 | 4 | VNI[c] | <1 | VNI | <1 |
| Placebo | | | | | | | | | | | |
| 95N009 | <4 | <4 | <4 | <4 | <4 | <4 | <4 | VNI | <1 | VNI | <1 |
| 95N163 | <4 | <4 | <4 | <4 | <4 | <4 | <4 | VNI | <1 | VNI | <1 |

B: Virologic and Immunologic Results of Samples collected from Rhesus Monkeys Vaccinated with either C3490 or C3605 HPIV2 Vaccine Candidate
Breakdown of Vero Plate Data for NW (positive samples only)

| Rhesus monkey # | Titer (pfu/mL), Day Post Inoculation | | | | | | | |
|---|---|---|---|---|---|---|---|---|
| | 0 | 3 | 5 | 7 | 10 | 12 | 14 | 17 |
| Pool 500 (PIV2, C3490,cp51) | | | | | | | | |
| 95N140 | <1 | <1 | 1.8 | 1.8 | 1.9 | <1 | <1 | <1 |
| 95N159 | <1 | <1 | <1 | 1.0* | <1 | <1 | 1.0* | <1 |
| 95N148 | <1 | <1 | <1 | <1 | <1 | <1 | <1 | 1.0* |
| Pool 502 (PIV2, C3605, cp47) | | | | | | | | |
| 95N152 | <1 | <1 | 1.0* | ≥1.5* | <1 | <1 | <1 | <1 |
| 95N147 | <1 | 1.0* | ≥1.5* | ≥1.5* | 1.7 | 1.4 | p[e] | <1 |
| 95N145 | <1 | 1.0* | 2.2 | 2.6 | 1.5 | <1 | <1 | <1 |

[a]NW = Nasal Wash
[b]BL = Bronchial Lavage
[c]VNI = Virus not Isolated
[d]HAI data from 5/21/98 for sera at all time points
*= titer based on RMK data, one positive tube = 1.0; two HA positive tube =≥ 1.5

TABLE 10

Samples from Rhesus Monkeys Vaccinated with Either Pool 502 or Placebo

| Rhesus Monkey ID# Pool 502 (PIV2, C3605,cp 47) | HPIV-2 Isolation from Vero Assay [Virus Titer(log pfu/mL)] | | | | | | | | | | | | HAI Titer | | | | | | |
|---|---|---|---|---|---|---|---|---|---|---|---|---|---|---|---|---|---|---|---|
| | Day Post Inoculation (NW[a]) | | | | | | Day Post Inoculation (BL[b]) | | | | | | Day Post Inoculation | | | | | | |
| | 0 | 3 | 5 | 7 | 10 | 12 | 0 | 3 | 5 | 7 | 10 | 12 | 0 | 7 | 14 | 21 | 28 | 42 | 56 |
| 95N024 | <1 | <1 | 1.5 | 1.8 | <1 | <1 | <1 | <1 | <1 | <1 | <1 | <1 | <4 | <4 | <4 | <4 | <4 | <4 | <4 |
| 95N087 | <1 | 1.5* | 1.0* | 1.2 | 2.0* | 1.0* | <1 | <1 | <1 | <1 | <1 | <1 | <4 | <4 | <4 | <4 | <4 | <4 | <4 |
| 95N138 | <1 | 1.5* | 1.0* | 2.0* | 1.0 (1.5*) | ≧1.5 | <1 | <1 | <1 | <1 | <1 | <1 | <4 | <4 | <4 | <4 | <4 | <4 | <4 |
| 95N181 | <1 | <1 | 1.5* | 2.5 | 2.0* | <1 | <1 | <1 | <1 | <1 | <1 | <1 | <4 | <4 | <4 | <4 | <4 | <4 | <4 |
| Placebo | | | | | | | | | | | | | | | | | | | |
| 95N006 | <1 | <1 | <1 | <1 | <1 | <1 | <1 | <1 | <1 | <1 | <1 | <1 | <4 | <4 | <4 | <4 | <4 | <4 | <4 |
| 95N009 | <1 | <1 | <1 | <1 | <1 | <1 | <1 | <1 | <1 | <1 | <1 | <1 | <4 | <4 | <4 | <4 | <4 | <4 | <4 |

[a]NW = nasal wash
[b]BL = Bronchial Lavage
*= titer based on RMK data, one positive tube = 1.0, two HA positive tubes =≧ 1.5

TABLE 11

Samples from Rhesus Monkeys Vaccinated with Either Pool 502 or Placebo and then Challenged with wild type HPIV2

| Rhesus Monkey ID# Pool 502 (wild type) (PIV2, C3605, cp47) | HPIV-2 Isolation from Vero Assay [Virus Titer(log pfu/mL)] | | | | | | | | | | | | HAI Titer | | | | | | |
|---|---|---|---|---|---|---|---|---|---|---|---|---|---|---|---|---|---|---|---|
| | Day Post Inoculation (NW[a]) | | | | | | Day Post Inoculation (BL[b]) | | | | | | Day Post Inoculation | | | | | | |
| | 0 | 3 | 5 | 7 | 10 | 12 | 0 | 3 | 5 | 7 | 10 | 12 | 0 | 7 | 14 | 21 | 28 | 42 | 56 |
| 95N024 | <1 | <1 | <1 | <1 | <1 | <1 | <1 | <1 | <1 | <1 | <1 | <1 | <4 | <4 | <4 | 4 | 8 | 8 | 4 |
| 95N087 | <1 | <1 | <1 | <1 | <1 | <1 | <1 | <1 | <1 | <1 | <1 | <1 | <4 | 64 | 128 | 128 | 64 | 64 | 64 |
| 95N138 | <1 | <1 | <1 | <1 | <1 | <1 | <1 | <1 | <1 | <1 | <1 | <1 | <4 | 256 | 512 | 512 | 256 | 128 | 128 |
| 95N181 | <1 | <1 | <1 | <1 | <1 | <1 | <1 | <1 | <1 | <1 | <1 | <1 | <4 | 256 | 128 | 128 | 64 | 32 | 32 |
| Placebo | | | | | | | | | | | | | | | | | | | |
| 95N006 | <1 | 1.9 | 1.5 | <1 | <1 | <1 | <1 | 1.0* | <1 | <1 | <1 | <1 | <4 | <4 | <4 | 32 | 32 | 32 | 16 |
| 95N009 | <1 | ≧1.5 | ≧1.5 | <1 | <1 | <1 | <1 | 1.0* | <1 | <1 | <1 | <1 | <4 | <4 | 4 | 8 | 16 | 16 | 32 |

[a]NW = nasal wash
[b]BL = Bronchial Lavage
*= titer based on RMK data, one positive tube = 1.0, two HA positive tubes =≧ 1.5

REFERENCES

Belshe, R. B., and Hissom, F. K. (1982). Cold adaption of parainfluenza virus type 3: Induction of three phenotypic markers. *J. Med. Virol.* 10, 235–242.

Belshe, R. B., Karron, R. A., Newman, F. K., Anderson, E. L., Nugent, S. L., Steinhoff, M., Clemens, M. L., Wilson, M. H., Hall, S. L., Tierney, E. L., and Murphy, B. R. (1992). Evaluation of a live attenuated, cold-adapted parainfluenza virus type 3 vaccine in children. *J. Clin. Microbiol.* 30, 2064–2070.

Clements, et al. 1991. Evaluation of bovine, cold-adapted human, and wild-type human parainfluenza type 3 viruses in adult volunteers and in chimpanzees. J. Clin. Microbiol. 29:1175–1182.

Collins, P. L., et al., p. 1205–1241, Vol. 1 of *Fields Virology*, Fields, B. N., et al., Eds., 3rd. ed., Raven Press, 1996.

Crookshanks-Newman and Belshe. 1986. Protection of weanling hamsters from experimental infection with wild-type parainfluenza virus type 3 (para 3) by cold-adapted mutants of para 3.J. Med. Virol. 18:131–137.

Downham, M. A., McQuillin, J., and Gardner, P. S. (1974). Diagnosis and clinical significance of parainfluenza virus infections in children. *Arch. Dis. Child.* 49, 8–15.

Glezen, W. P., and Femald, G. W. (1976). Effect of passive antibody on parainfluenza virus type 3 pneumonia in hamsters. *Infect. Immun.* 14, 212–216.

Gross, P. A., Green, R. H., and McCrearren, M. G. (1973). Persistent infection with parainfluenza type 3 virus in man. *Am. Rev. Respir. Dis.* 108, 894–898.

Hall, S. L., Sarris, C. M., Tiemey, E. L., London, W. T., and Murphy, B. R. (1993). A cold-adapted mutant of parainfluenza virus type 3 is attenuated and protective in chimpanzees. *J. Infect. Dis.* 167, 958–962.

Henrickson, K. J., Kuhn, S. M., and Savatski, L. L. (1994). Epidemiology and cost of infection with human parainfluenza virus types 1 and 2 in young children. *Clin. Infect. Dis.* 18, 770–779.

Hu, X., Ray, R., and Compans, R. W. (1992). Functional interactions between the fusion protein and hemagglutinin-neuraminidase of human parainfluenza viruses. *J. Virol.* 66, 1528–1534.

Karron, R. A., Wright, P. F., Newman, F. K., Makhene, M., Thompson, J., Samorodin, R., Wilson, M. H., Clemens, M. L., Murphy, B. R., and Belshe, R. B. (1995). A live attenuated human parainfluenza type 3 virus vaccine is safe, infectious, immunogenic and phenotypically stable in healthy infants and children. *J. Infect. Dis.* 172, 1445–1450.

Kingsbury, D. W. (1991). The paramyxoviruses. Plenum, New York.

Matsouka, Y., Curran, J., Pelet, T., Kolafsky, D., Ray, R., and Compans, R. W. (1991). The P gene of human parainfluenza virus type 1 encodes P and C proteins but not a cysteine-rich V protein. *J. Virol.* 65, 3406–3410.

Parkinson, A. J., Muchmore, H. G., McConnell, T. A., Scott, L. V., and Miles, J. A. R. (1980). Serological evidence for parainfluenza virus infection during isolation at South Pole Station, Antarctica. *Am. J. Epidemiol.* 112, 334–340.

Ray, R., and Compans, R. W. (1990). Immunochemistry of paramyxoviruses. In "Immunochemistry of Viruses II" (M. V. H. Van Regemnortel and A. R. Neurath, eds.), pp. 215–234. Elsevier, Amsterdam.

Sarkkinen, H. K., Halonen, P. E., and Salmi, A. A. (1981). Type-specific detection of parainfluenza viruses by enzyme-immunoassay and radioimmunoassay in nasopharyngeal specimens of patients with acute respiratory disease. *J. Gen. Virol.* 56, 49–57.

Storey, D. G., Dimock, K., and Kang, C. Y. (1984). Structural characterization of virion proteins and genomic RNA of human parainfluenza virus 3. *J. Virol.* 52, 761–766.

Welliver, R. C., Wong, D. T., Middleton, E. J., Sun, M., McCarthy, N., and Ogra, P. L. (1982). Role of parainfluenza virus-specific IgE in pathogenesis of croup and wheezing subsequent to infection. *J. Pediatr.* 101, 889–896.

We claim:

1. An isolated, attenuated viral strain of human parainfluenza virus 2, wherein the viral strain is temperature sensitive and cold adapted.

2. The isolated, attenuated viral strain of claim 1 which exhibits titers in plaque assays on Vero cells when grown at around 32° C. in a mammalian host cell which are less about 100 times its titer when grown at around 23° C. in the mammalian host cell, and which are greater than or equal to about 100 times its titer when grown at around 39° C. in the mammalian host cell.

3. The isolated, attenuated viral strain of claim 1 which exhibits titers in plaque assays on Vero cells when grown at around 39° C. in the mammalian host cell which are less than or equal to about 1.0 pfu/ml.

4. The isolated, attenuated viral strain of claim 1 which is selected from the group of viral strains consisting of those designated C3464, C3490, C3605, and subclones or progeny of any of the aforementioned strains.

5. A vaccine composition comprising the isolated, attenuated viral strain of claim 1 and a pharmaceutically acceptable carrier.

6. The vaccine composition of claim 5 further comprising a pharmaceutically acceptable excipient.

7. The vaccine composition of claim 5 further comprising a pharmaceutically acceptable adjuvant.

8. The vaccine composition of claim 5 wherein the isolated, attenuated viral strain exhibits titers in plaque assays on Vero cells when grown at around 32° C. in a mammalian host call which are less than about 100 times its titer when grown at around 23° C. in the mammalian host cell, and which are greater than or equal to about 100 times its titer when grown at around 39° C. in the mammalian host cell.

9. The vaccine composition of claim 8 further comprising a pharmaceutically acceptable excipient.

10. The vaccine composition of claim 8 further comprising a pharmaceutically acceptable adjuvant.

11. The vaccine composition of claim 5 wherein the isolated, attenuated viral strain is selected from the group of viral strains consisting of those designated C3464, C3490, C3605, and subclones or progeny of any of the aforementioned strains.

12. The vaccine composition of claim 11 further comprising a pharmaceutically acceptable excipient.

13. The vaccine composition of claim 11 further comprising a pharmaceutically acceptable adjuvant.

14. A method of inducing a protective immune response ma mammal comprising administering to the mammal an amount of the isolated, attenuated viral strain of claim 1 sufficient to elicit the protective immune response.

15. The method of claim 14 wherein the isolated, attenuated viral strain exhibits titers in plaque assays on Vero cells when grown at around 32° C. in a mammalian host cell which are less than about 100 times its titer when grown at around 23° C. in the mammalian host cell, and which are greater than or equal to about 100 times its titer when crown at around 39° C. in the mammalian host cell.

16. The method of claim 14 wherein the isolated, attenuated viral strain exhibits titers in plaque assays on Vero cells when crown at around 39° in the mammalian host cell which are less than or equal to about 1.0 pfu/ml.

17. The method of claim 14 wherein the isolated, attenuated viral strain is selected from the group of viral strains consisting of those designated C3464, C3490, C3605, and subclones or progeny of any of the aforementioned strains.

18. The isolated, attenuated viral strain of claim 1, wherein the viral strain is produced by a method comprising the steps of:
  (a) culturing in vitro a wild type human parainfluenza virus 2 (HPIV-2);
  (b) cold passaging said virus at a first temperature;
  (c) selecting viruses that grow at the first temperature;
  (d) cold passaging the selected viruses at a second temperature, the second temperature being less than the first; and
  (e) selecting viruses that grow at the second temperature.

19. The isolated, attenuated viral strain of claim 18, further comprising the steps of:
  (f) cold passaging the selected viruses at a third temperature, the third temperature being less than the second; and
  (g) selecting viruses that grow at the third temperature.

20. The isolated, attenuated viral strain of claim 19, further comprising the steps of:
  (h) cold passaging the selected viruses at a fourth temperature, the fourth temperature being less than the third; and
  (i) selecting viruses that grow at the fourth temperature.

21. The isolated, attenuated viral strain of claim 18, wherein the virus is passaged and selected more than once at each temperature.

22. The isolated, attenuated viral strain of claim 20, wherein the virus is passaged and selected more than once at each temperature.

23. The isolated, attenuated viral strain of claim 22, wherein the viruses are passaged at a first temperature of about 30° C., at a second temperature of about 28° C., at a third temperature of about 26° C., and at a fourth temperature of about 24° C.

24. The isolated, attenuated viral strain of claims 23, wherein the viruses are passaged six times at 30° C., six times at 28° C., eight times at 26° C. and thirteen times at 24° C.

25. A vaccine composition comprising the isolated, attenuated viral strain of claim 18 and a pharmaceutically acceptable carrier.

26. A vaccine composition comprising the isolated, attenuated viral strain of claim 20 and a pharmaceutically acceptable carrier.

27. A method of inducing a protective immune response in a mammal comprising administering to the mammal an amount of the isolated, attenuated viral strain of claim 18 sufficient to elicit the protective immune response.

28. A method of inducing a protective immune response in a mammal comprising administering to the mammal an amount of the isolated, attenuated viral strain of claim 20 sufficient to elicit the protective immune response.

29. A method of producing an isolated, attenuated viral strain of human parainfluenza virus 2, wherein the viral strain is temperature sensitive and cold adapted, the method comprising the steps of:

(a) culturing in vitro a wild type human parainfluenza virus 2 (HPIV-2);

(b) cold passaging said virus at a first temperature;

(c) selecting viruses that grow at the first temperature;

(d) cold passaging the selected viruses at a second temperature; the second temperature being less than the first; and e) selecting viruses that grow at the second temperature.

30. The method according to claim 29, further comprising the steps of:

(f) cold passaging the selected viruses at a third temperature, the third temperature being less than the second; and (g) selecting viruses that grow at the third temperature.

31. The method according to claim 30, further comprising the steps of:

(h) cold passaging the selected viruses at a fourth temperature, the fourth temperature being less than the third; and (i) selecting viruses that grow at the fourth temperature.

32. The method according to claim 29, wherein the virus is passaged and selected more than once at each temperature.

33. The method according to claim 31, wherein the virus is passaged and selected more than once at each temperature.

34. The method according to claim 33, wherein the viruses are passaged at a first temperature of about 30° C., at a second temperature of about 28° C., at a third temperature of about 26° C., and at a fourth temperature of about 24° C.

35. The method according to claim 34, wherein the viruses are passaged six times at 30° C., six times at 28° C., eight times at 26° C. and thirteen times at 24° C.

36. The method according to claim 35, wherein the isolated, attenuated viral strain exhibits titers in plaque assays on Vero cells when grown at around 32° C. in a mammalian host cell which are less than about 100 times its titre when grown at around 23° C. in the mammalian host cell, and which are greater than or equal to about 100 times its titre when grown at around 39° C. in the mammalian host cell.

37. The method according to claim 36, wherein the isolated attenuated viral strain exhibits titers in plaque assays on Vero cells when grown at around 39° C. in the mammalian host cell which are less than or equal to about 1.0 pfu/ml.

* * * * *

UNITED STATES PATENT AND TRADEMARK OFFICE
CERTIFICATE OF CORRECTION

PATENT NO. : 6,946,136 B2  Page 1 of 1
DATED : September 20, 2005
INVENTOR(S) : Robert B. Belshe et al.

It is certified that error appears in the above-identified patent and that said Letters Patent is hereby corrected as shown below:

<u>Title page,</u>
Item [*] Notice, delete "by 993 days" and insert -- by 718 days --.

<u>Column 20,</u>
Lines 18-19, "response ma mammal" should read -- response in a mammal --.
Lines 28 and 31, "crown" should read -- grown --.

Signed and Sealed this

Twenty-eighth Day of March, 2006

JON W. DUDAS
*Director of the United States Patent and Trademark Office*